US011123115B2

(12) United States Patent
Verstreken et al.

(10) Patent No.: US 11,123,115 B2
(45) Date of Patent: Sep. 21, 2021

(54) ORTHOPEDIC BONE FIXATION SYSTEMS AND METHODS

(71) Applicants: MATERIALISE N.V., Leuven (BE); Frederik Verstreken, Schoten (BE)

(72) Inventors: Frederik Verstreken, Schoten (BE); Wilfried Vancraen, Huldenberg (BE); Bram Lenaerts, Pulle (BE)

(73) Assignee: Materialise N.V., Leuven (BE)

( * ) Notice: Subject to any disclaimer, the term of this patent is extended or adjusted under 35 U.S.C. 154(b) by 114 days.

(21) Appl. No.: 15/993,985

(22) Filed: May 31, 2018

(65) Prior Publication Data

US 2018/0271569 A1    Sep. 27, 2018

Related U.S. Application Data

(63) Continuation of application No. 14/518,647, filed on Oct. 20, 2014, now abandoned, which is a
(Continued)

(51) Int. Cl.
*A61B 17/80* (2006.01)
*A61B 17/15* (2006.01)
(Continued)

(52) U.S. Cl.
CPC ............ *A61B 17/80* (2013.01); *A61B 17/151* (2013.01); *A61B 17/809* (2013.01); *G06F 19/00* (2013.01);
(Continued)

(58) Field of Classification Search
CPC .. A61B 17/80–8095; A61B 17/82–826; A61B 34/10; A61B 2034/101–108
(Continued)

(56) References Cited

U.S. PATENT DOCUMENTS 6,711,432 B1 *   3/2004   Krause ................... A61B 17/15
                                                              128/922
8,568,462 B2   10/2013   Sixto, Jr. et al.
(Continued)

FOREIGN PATENT DOCUMENTS

EP        0908836 A2    4/1999
FR     2 709 410 A1    3/1995
(Continued)

OTHER PUBLICATIONS

International Search Report dated Jul. 30, 2013, for related application PCT/EP2013/058041 filed Apr. 18, 2013.

*Primary Examiner* — Matthew J Lawson
(74) *Attorney, Agent, or Firm* — Patterson + Sheridan, LLP (57) ABSTRACT

The orthopedic systems are patient-specific and provided with two types of features for positioning and/or fixing the plate to the bone or bone fragments. A method for generating bone plates comprises: generating a model of the bone defect or envisaged osteotomy based on one or more images of the bone and the surgical plan; designing based on said model a model corresponding to the envisioned repair of said bone defect/envisaged result of the osteotomy; generating a bone plate based on the information above, comprising: one or more patient-specific features corresponding to the surface of a bone fragment in the area close to the defect; and one or more fixation features whose position and/or orientation is such that the fixation elements will enter the bone in areas suitable for fixing the bone plate to each bone fragment.

9 Claims, 4 Drawing Sheets

Related U.S. Application Data continuation of application No. PCT/EP2013/058041, filed on Apr. 18, 2013.

(60) Provisional application No. 61/625,819, filed on Apr. 18, 2012.

(51) Int. Cl.
| | | |
|---|---|---|
| *G16H 50/50* | (2018.01) | |
| *A61B 34/10* | (2016.01) | |
| *G06F 19/00* | (2018.01) | |
| *A61B 17/00* | (2006.01) | |

(52) U.S. Cl.
CPC .... *G16H 50/50* (2018.01); *A61B 2017/00526* (2013.01); *A61B 2034/102* (2016.02); *A61B 2034/108* (2016.02)

(58) Field of Classification Search
USPC .................................................. 606/283–285
See application file for complete search history.

(56) References Cited

U.S. PATENT DOCUMENTS

| | | | | |
|---|---|---|---|---|
| 8,939,984 | B2* | 1/2015 | Budoff | A61B 17/152 606/87 |
| 10,849,632 | B2* | 12/2020 | Wu | A61B 17/152 |
| 10,898,211 | B2* | 1/2021 | Fallin | A61B 17/8061 |
| 10,925,652 | B2* | 2/2021 | Pavlov | A61B 17/157 |
| 2004/0068187 | A1* | 4/2004 | Krause | A61B 17/15 600/443 |
| 2004/0153073 | A1 | 8/2004 | Orbay | |
| 2006/0161158 | A1 | 7/2006 | Orbay et al. | |
| 2007/0173815 | A1* | 7/2007 | Murase | A61B 17/15 606/53 |
| 2007/0233114 | A1 | 10/2007 | Bouman | |
| 2007/0238069 | A1 | 10/2007 | Lovald et al. | |
| 2008/0195240 | A1* | 8/2008 | Martin | A61B 17/8061 700/98 |
| 2009/0204121 | A1 | 8/2009 | Cavallazzi et al. | |
| 2009/0281543 | A1 | 11/2009 | Orbay et al. | |
| 2010/0069966 | A1 | 3/2010 | Castaneda et al. | |
| 2010/0152782 | A1* | 6/2010 | Stone | A61B 17/809 606/280 |
| 2011/0092981 | A1 | 4/2011 | Ng et al. | |
| 2011/0093018 | A1 | 4/2011 | Prasad et al. | |
| 2011/0118770 | A1 | 5/2011 | Pokorney et al. | |
| 2011/0213376 | A1* | 9/2011 | Maxson | A61B 17/151 606/88 |
| 2011/0264100 | A1 | 10/2011 | Sixto, Jr. et al. | |
| 2011/0288640 | A1 | 11/2011 | Lal | |
| 2012/0130383 | A1* | 5/2012 | Budoff | A61B 17/152 606/87 |
| 2012/0303033 | A1* | 11/2012 | Weiner | A61B 17/8061 606/87 |
| 2016/0287335 | A1* | 10/2016 | Goto | A61B 17/17 |
| 2020/0040532 | A1* | 2/2020 | Sealey, II | D21F 11/145 |
| 2020/0352582 | A1* | 11/2020 | Larche | A61B 17/1728 |
| 2020/0388085 | A1* | 12/2020 | Furnstahl | A61B 17/808 |
| 2021/0022879 | A1* | 1/2021 | Hollis | A61B 17/151 |
| 2021/0085346 | A1* | 3/2021 | Awtrey | A61B 17/1796 |

FOREIGN PATENT DOCUMENTS

| | | |
|---|---|---|
| GB | 2 243 316 A | 10/1991 |
| WO | 2007/045000 A2 | 4/2007 |
| WO | WO-2013053614 A1 * 4/2013 | ............ A61B 34/10 |

* cited by examiner

ORTHOPEDIC BONE FIXATION SYSTEMS AND METHODS

CROSS-REFERENCE TO RELATED APPLICATIONS

The present application is a continuation of U.S. application Ser. No. 14/518,647, filed Oct. 20, 2014, which is a continuation under 35 U.S.C. § 120 of International Application No. PCT/EP2013/058041, filed Apr. 18, 2013 (and published on Oct. 24, 2013 in English by the International Bureau as International Publication No. WO 2013/156545), which claims priority to U.S. Provisional Application No. 61/625,819, filed Apr. 18, 2012. The entire contents of each of the above-referenced patent applications are hereby incorporated by reference.

FIELD OF THE INVENTION

The present application relates to orthopedic bone fixation systems and methods for performing orthopedic interventions according to pre-operative planning. The orthopedic systems can be patient-specific.

BACKGROUND

The human skeleton is composed of a large number of individual bones that perform a variety of important functions, including support, movement, protection, storage of minerals, and formation of blood cells. In response to trauma bones of the skeleton may become fractured. To ensure that the skeleton retains its ability to perform its important functions and to reduce pain and disfigurement, fractured bones should be repaired promptly and properly. Typically, fractured bones are treated using fixation devices, which reinforce the fractured bones and keep them aligned during healing. Fixation devices may take a variety of forms, including casts for external fixation and bone plates for internal fixation. Casts are minimally invasive, allowing reduction and fixation of simple fractures from outside the body. In contrast, bone plates are sturdy internal devices that are mounted directly onto the bone(s) adjacent to the fracture.

Some bone defects (such as hallux valgus, coxa vara, genu valgum, and genu varum) are treated by an osteotomy, i.e. a surgical intervention involving cutting of the bone in order to shorten the bone, lengthen it or change its alignment. After surgery a bone plate is often used to hold the remaining detached bone fragments in their desired position for healing.

Bone plates generally provide a rigid structure comprising openings through which bone fixation elements are inserted into the bone to anchor the plate to the target portions of the bone. The bone plate is fastened to opposite sides of the fracture or surgical cut using suitable fixation elements, such as screws and/or wires, so that the bone fragments are fixed in position. The mounted plate may be left in place permanently, or it may be removed after the bone has healed sufficiently.

Bone plates are available in different sizes such that the surgeon can choose a bone plate adapted to the size of the fracture and/or disconnected bone fragments during the surgical procedure. However, the shape of the bone plates from which the surgeon can choose is limited, as the currently available bone plates typically have a generic shape. A suboptimal fit of the bone plate however may negatively affect the healing process.

Another problem often encountered during these types of orthopedic procedures is that during the fixation of the bone plate the fracture dislocates or repositions slightly due to the forces required for inserting the fixation elements into the bones for fastening the bone plate. As there is almost no opportunity during the surgical procedure to loosen the fixation elements in order to reposition the fracture for optimal healing, small dislocations are often left, leading to suboptimal healing of the fracture and possible complications during or after the healing process.

Accordingly, there is a need for improved ways to repair structural defects in the field of orthopedic surgery.

SUMMARY

Provided herein are orthopedic devices which allow fixation of two or more partially or entirely disconnected bone fragments according to a pre-operatively determined position relative to each other and methods for placing such orthopedic devices.

More particularly, disclosed herein is a bone plate for use in orthopedic surgery for fixating two or more bone fragments according to a pre-operative plan, comprising: a rigid structure comprising one or more patient-specific features allowing the positioning of the bone plate onto at least one bone fragment in a specific position which position is determined based on pre-operative planning; fixation features for fixing the bone plate onto the bone or bone fragments; and positioning elements which aid the positioning of the bone plate onto the bone.

More particularly, said bone plate is a bone plate for fixing two bone fragments to each other, wherein the bone plate comprises at least two patient-specific features, each corresponding to or matching a feature on one of the bone fragments which are to be fixed together. More particularly, the patient-specific features are selected such that in the pre-operatively determined correct relative position of the bone fragments, the patient-specific features on the bone plate optimally match the corresponding features on the bone fragments.

More particularly, said bone plate provided is a bone plate wherein the rigid structure which is the supporting element may vary in thickness. In further particular embodiments, the rigid structure of the bone plate is locally increased around the osteotomy or fracture plane of the bone fragments.

In particular embodiments, bone plates are provided wherein the positioning elements are non-threaded structures extending from the rigid structure of the bone plate, such as, but not limited to pins, pegs or hooks. Additionally or alternatively, the positioning elements may be structures holes for positioning devices such as are non-threaded pin-, peg- or hook-like structures. Optionally, the positioning elements may be detachable from the bone plate rigid structure.

In particular embodiments, the fixation elements are threaded holes for screws.

The position and orientation of the positioning elements and fixation features are determined according to a pre-operative plan.

The application further provides guides for drilling holes into bone fragments corresponding to the desired position of the screws which are introduced in the fixation features of a bone plate for fixing said bone fragments. More particularly, the application envisages combinations of a bone plate for fixing onto two bone fragments or a defect bone area as described herein comprising a rigid structure, one or more patient-specific features and fixation features and a guide for drilling holes into the bone or bone fragments in pre-operatively planned position of the fixation elements.

In particular embodiments, bone plates are provided which comprise two or more separate parts, each comprising a rigid structure with one or more fixation features and optionally one or more positioning elements, which can be combined and attached to each other to form a one-piece bone plate after placement on the bone fragments and positioning the bone fragments in the pre-operatively planned position.

In a further particular embodiment, methods are provided for generating bone plates providing a tailored and defect-specific approach comprising the steps of: generating a 2-dimensional (2D) or 3-dimensional (3D) model of the bone defect or envisaged osteotomy based on one or more images of the bone and the surgical plan; designing, based on said 2D or 3D model, a model corresponding to the envisioned repair of said bone defect/envisaged result of the osteotomy; generating a bone plate with a rigid structure based on the information above comprising: one or more patient-specific features matching or corresponding to the surface of a bone fragment in the area close to the defect, and one or more fixation features whereby the position and orientation is selected based on the information above so as to be suitable for fixing the bone plate to said bone fragments.

More particularly, methods are provided for generating a guide for a bone plate as described herein, the method comprising, determining, based on the pre-operative plan the desired positions of the holes for the fixation of the bone plate to the bone fragments, and generating a guide comprising drill-guides for drilling holes in to the bone or bone fragments to receive the fixation elements (such as screws) introduced through the fixation features of the bone plate. More particularly the methods for generating the bone plate (and optionally the guide) involve performing virtual surgery on the defective bone to identify the defect site and determining the shape and/or form parameters of the defect or of the structure necessary to fix the defect.

In a further particular embodiment, a method is provided for fixating bone fragments according to a predetermined position comprising the steps of: drilling holes into the bone or bone fragments, for receiving the fixation elements; repositioning the bone fragments into the correct position for healing, positioning a bone plate as disclosed herein on the bone fragments using the positioning elements; and introducing fixation elements into the fixation features on the bone plate, thereby fixing the bone fragments or bone according to a predetermined position.

More particularly, the method comprises first a step of positioning a bone plate as disclosed herein on one of the bone fragments, followed by repositioning the bone fragments into the correct position for healing using the bone plate fixed onto one of the bone fragments as a hinge and further positioning the bone plate onto the bone fragments.

The application further claims kits comprising tools for performing at least part of the surgical procedures described herein. In particular embodiments the kits comprise: a patient specific bone plate as disclosed herein; and a guide for drilling holes corresponding to the desired location and direction of the fixation elements, which are to be introduced through the fixation features of the bone plate.

More particularly, the kits may further comprise positioning devices which fit into a positioning feature of the bone plate and/or fixation elements corresponding to the fixation features on the bone plate for further fixing the bone plate into the correct position on the bone fragments.

BRIEF DESCRIPTION OF THE DRAWINGS

The following description of a specific embodiment is merely exemplary in nature and is not intended to limit the present teachings, their application or uses.

The following references are used throughout the figures: bone (1), bone plate (2), bone plate supporting structure (3), bone plate positioning elements (4), bone plate fixation features (5), fixation elements (6), patient-specific features (7), drill guide (10), K-wire (11), hole (12), cutting guide (13) and bone osteotomy (14).

DETAILED DESCRIPTION OF CERTAIN INVENTIVE EMBODIMENTS

The disclosed systems and methods as described herein will be described with respect to particular embodiments but the systems and methods are not limited thereto.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited members, elements or method steps also include embodiments which "consist of said recited members, elements or method steps.

Furthermore, the terms first, second, third and the like in the description, are used for distinguishing between similar elements and not necessarily for describing a sequential or chronological order, unless specified. It is to be understood that the terms so used are interchangeable under appropriate circumstances and that the embodiments described herein are capable of operation in other sequences than described or illustrated herein.

All documents cited in the present specification are hereby incorporated by reference in their entirety.

Unless otherwise defined, all terms used herein, including technical and scientific terms, have the meaning as commonly understood by one of ordinary skill in the art. By means of further guidance, definitions for the terms used in the description are included to better appreciate the present teaching. The terms or definitions used herein are provided solely to aid in the understanding of the present disclosure.

Reference throughout this specification to "one embodiment" or "an embodiment" means that a particular feature, structure or characteristic described in connection with the embodiment is included in at least one embodiment as disclosed herein. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the present scope, and form different embodiments, as would be understood by those in the art.

Provided herewith are systems, including apparatuses and methods which may be used for performing a surgical orthopedic intervention requiring the installation of a bone plate, allowing the surgeon to perform the orthopedic intervention according to a preoperative plan to ensure accuracy of the intervention such that the amount of time the patient is in surgery is minimized and the post-operative healing process is optimized. The orthopedic systems can be patient-specific.

A first aspect relates to a bone plate for use in the context of orthopedic surgery. The bone plate is used for fixating two or more bone fragments according to a preoperative plan. A bone fragment as used herein refers to partially or completely separated parts originating from one bone. The bone plate ensures that the bone fragments are fixed in a predetermined position relative to each other to assist in the healing and/or to stabilize damaged or weakened bones or portions of bone.

The bone plate provides a rigid structure which is typically (but not necessarily) longitudinal in order to span over a gap (caused by fracture and/or osteotomy) between two bone fragments or over a stretch of weakened bone. The rigid structure, also referred to as supporting element, is such that, after attachment to the bone or bone fragments it can maintain these in position even under stress conditions.

The rigid structure of the bone plate typically comprises one or more patient-specific features, which allow positioning of the bone plate onto at least one bone fragment in a specific position which position is determined based on pre-operative planning. The one or more patient-specific features typically match features and/or areas of the bone or bone fragment(s) and help guide the placement of the bone plate and ensure a unique fit thereof. In particular embodiments the bone plate is envisaged for fixing two bone fragments to each other and comprises at least two patient-specific features, each corresponding to or matching a feature on one of the bone fragments which are to be fixed together whereby the features are selected such that in the pre-operatively determined relative position of the bone fragments, the features on the bone plate will optimally match the corresponding features on the bone fragments. Thus, the patient-specific features will help ensure that the bone plate fixes the bone fragments according to the pre-operative planning.

The rigid structure or supporting element of the bone plate may have a standard thickness or may be provided in a particular embodiment with a varying thickness. More particularly, the thickness of the supporting element may be locally increased for instance around the osteotomy or fracture plane, thereby to providing the bone plate with a higher stress resistance.

The patient-specific features provided on the bone plate are typically selected from patient-specific surfaces (matching a specific surface structure on the bone), combinations of specifically placed holding pins (corresponding to a specific shape of the bone), etc.

The bone plate further comprises fixation features for fixing the bone plate onto the bone or bone fragments. The fixation features typically comprise openings in the bone plate through which bone fixation elements, such as pins, but more particularly threaded elements such as screws can be inserted into the bone to anchor the bone plate to the bone.

In particular embodiments, the bone plate further comprises positioning elements which aid the positioning of the bone plate onto the bone. The positioning elements that are provided onto the bone plate may be any means which allow a first positioning of the bone plate onto the bone. In a particular embodiment, these positioning elements are non-threaded structures such as, but not limited to pins, pegs or hooks. The bone plates are typically provided with at least one positioning element, which is provided (or envisaged to be provided) on a part of the bone plate envisaged to be positioned on one of the bone fragments (where the fixation of more than one bone fragment is envisaged) or on one area of the bone. In particular embodiments, the bone plate comprises at least two positioning elements, the first positioning element being located on one bone fragment or part of the bone adjacent the bone defect or cut and the second positioning element being located on the other bone fragment or bone area adjacent to the bone defect or cut.

In particular embodiments however, one or more of the positioning elements may be non-threaded apertures such as, but not limited to holes for pins, pegs or hooks. Where the positioning element on the plate is a hole (extending through the rigid structure of the bone plate) for a pin peg or hook, this is intended for use with a corresponding external positioning device, such as a pin, peg or hook, which can be introduced through the bone plate into the bone upon positioning the bone plate. Typically, the position and orientation of the hole or opening will determine the orientation of the positioning device in the bone. Additionally or alternatively, in particular embodiments, the positioning element may be a structure extending from the rigid structure of the bone plate, which can be introduced into bone when positioning the bone plate onto a bone fragment e.g. by exerting pressure onto the bone plate. In these embodiments, the positioning element may have a pin, peg or hook-like shape extending from the bone plate (more particularly from the surface intended to be positioned on the bone, i.e. the same surface of the bone plate comprising the patient-specific feature(s)). Typically, as the bone plate is typically designed to be positioned parallel to the bone surface, the (external or incorporated) positioning elements/devices may be positioned perpendicular to the bone surface. This may imply that the positioning elements/devices intended for introducing into the bone are all positioned essentially perpendicular to the surface of the bone plate and to the surface of the bone. In particular embodiments, at least two of the positioning elements/devices are such that these elements/devices for introducing into the bone are positioned in parallel relative to each other. In further particular embodiments all positioning elements/devices of said bone plate are positioned parallel relative to each other. However, it is also envisioned that the positioning elements or external positioning devices are provided on the bone plate so as not to be positioned parallel to each other. This may increase the stability of the bone plate on the bone. In particular embodiments, the positioning elements are envisaged to be oriented at a slight angle (2-10°) with respect to the axis perpendicular to the bone surface. In particular embodiments, the orientation of this angle is different for the different positioning elements/devices. Where the positioning elements are openings which allow the introduction of external positioning devices, the openings can be provided such that they allow and/or ensure non-parallel introduction of external positioning devices. The same applies to the fixation features and their respective fixation elements.

In particular embodiments the positioning elements of said bone plate are detachable and removable, thereby allowing a first set of less permanent positioning elements to be removed and replaced by more permanent fixation elements. Thus, in particular embodiments, the positioning elements may function as fixation features. For instance, when pegs are used as positioning elements or positioning devices, after the positioning of the bone plate into the correct position and a first fixation of the bone plate to the bone, one may envisage removing the pegs from the bone plate and introducing further screws as fixation elements to further strengthen the position of the bone plate. In particular embodiments as detailed above, the bone plate is thus provided with a combination of fixed positioning elements on the bone plate which are openings and separate external positioning devices and fixation elements which can be inserted there through.

It will be understood that the bone plates are tailored specifically for the repair of the bone defect or osteotomy at hand. In particular embodiments, not only patient-specific features are provided, but the size of the bone plate and the position and orientation of the different positioning elements and fixation features are determined according to a preoperative plan.

According to particular embodiments, a multitude of 3, 4, 5, 6, 7, 8 or more fixation features and/or positioning elements can be provided on the bone plate, depending on the complexity of the bone defect (where multiple parts are to be fixated relative to each other with one bone plate) or where for instance a higher degree of strength is required.

The present disclosure further envisages methods for fixing bone fragments according to a predetermined position using the bone plates as disclosed herein.

These methods typically involve the step of drilling holes into the bone or bone fragments, for receiving the positioning elements and/or the fixation elements introduced through the fixation features of the bone plate. Thus, holes to receive these positioning elements and/or fixation elements are drilled into the bone or bone fragments according to a pre-operatively planned position of the bone plate. Drilling of the holes is typically ensured using a guide.

Where the bone plate as disclosed herein is envisaged for use in an osteotomy procedure of an intact bone, e.g. for removing part of the bone, drilling of the holes can be ensured prior to the osteotomy step, i.e. when the bone is still in one piece. Alternatively, drilling can be ensured after the osteotomy is performed, on each of the bone fragments.

Thereafter, the bone plate is positioned on one of the bone fragments. More particularly, the part of the bone plate envisaged for placement on that bone fragment.

In particular embodiments, the bone plate is provided with at least one patient-specific feature matching an area of that bone fragment to which the bone plate is attached first. More particularly, the patient-specific feature matches an area of the bone fragment to which the bone plate is first attached near or adjacent to the areas where the positioning elements and/or fixation elements are or will be introduced into the bone fragment. By providing patient-specific features near areas where positioning elements and/or fixation elements are introduced, the surgeon manipulating and positioning the patient-specific bone plate is ensured that the bone plate is fixed in the correct position when fixing the bone plate onto the patient's anatomy.

In particular embodiments, after the bone plate has been fixed onto the first bone fragment, the two or more bone fragments are repositioned into the correct position for healing, using the bone plate fixated onto one of the bone fragments as a hinge to aid the surgeon. Where the bone plate comprises a further patient-specific feature corresponding to/matching a feature on the surface of the second bone fragment, the correct fit of the bone plate on the second bone fragment will be aided by matching the patient-specific feature with the corresponding feature on the bone.

Once the bones are placed in the correct relative position for healing the fixation elements can be introduced into the fixation features on the bone plate through the bone, thereby fixating the position of the reconstituted bone defect in the correct position for optimal healing.

As the bone plate is used as a hinge for repositioning the bone fragments into to their correct relative position for healing, it may be necessary to ensure a fixation to the first bone fragment which is sufficiently strong. The provision of multiple positioning elements on the bone fragment to which the bone plate is first attached provide an increased strength of the attachment and allows the surgeon to put more pressure on the bone plate which functions as a hinge. Accordingly, the number of positioning elements on either side of the bone plate may be unequal, thereby providing N+X positioning elements on the side of the bone plate which is fixated first to the bone fragment and providing N positioning elements on the side of the bone plate which is fixated once the bone defect is repositioned into the correct position for healing, N being an integer equal to 1, 2, 3, 4, 5, 6, 7, 8 or more and X being an integer equal to 1, 2, 3, 4, 5, 6, 7, 8 or more. In particular embodiments the positioning elements are an integral part of the bone plate.

Once the bone fragments are repositioned and the bone plate is fixated into the correct position using the positioning elements, the bone plate is fastened to the different bone fragments using suitable fixation elements. Suitable fixation elements include any type of fixation or attachment elements as can be envisaged by a skilled person, including, but not limited to screw, nails, bolts, pins, clamps or stitches, to ensure that the bone plate is definitively fixed into position.

As described above, the bone plate comprises fixation features such as openings through which bone fixation elements can be inserted into the bone to definitely anchor the bone plate to each of the bone fragments. As the bone plate is already fixated into the correct position (by the positioning elements), the further fixation using stronger and more permanent fixation elements will not have an effect on the position of the reconstituted bone, thereby ensuring that the correct position for healing is maintained also after fixating the bone plate permanently. The mounted bone plate may be left in place permanently, or it may be removed after the bone has healed sufficiently.

It is noted that typically the bone plate as disclosed herein is a one piece structure optionally with separate or detachable fixation and/or positioning elements.

In an alternative embodiment the bone plate is provided in two or more separate parts, which can be combined and attached to each other to form a one-piece bone plate after placement on the bone fragments. In these embodiments, the complete bone plate (i.e. when both parts are joined) is designed according to pre-operative planning to ensure correct positioning of the different bone fragments relative to each other. The bone plate is however provided in two parts, each of which can be attached to a bone fragment in a specific position (optionally guided by one or more patient-specific features). Thereafter, connecting of the two parts of the bone plate (to generate a single base plate structure) will ensure that the corresponding bone fragments are correctly positioned.

In particular embodiments the separate parts of the bone plate each comprise positioning elements. In these embodiments, the two parts of the bone plate can be referred to as positioning parts. In further particular embodiments, a positioning part comprises positioning elements provided with a patient-specific feature, ensuring/aiding the correct positioning of the positioning part onto a bone fragment. Typically, the positioning parts further comprise attachment elements to which a bone connector can be attached for connection of one positioning part to another.

Where the bone plate is provided as separate positioning parts, placement will typically first involve positioning of a positioning part on the bone and a first fixation by positioning elements. Typically, each of the two positioning parts is provided onto a different bone fragment. After inserting the positioning elements into the bone fragments, the bone fragments can be repositioned into the correct position relative to each other for healing. In a next step, the bone connector is attached to each of the positioning parts, thereby forming a bone plate as disclosed herein. By using a bone plate comprising separate parts which can be interconnected, the bone plate can be assembled by the surgeon during the surgical procedure, allowing the surgery to occur in a small surgical window, leading to a faster healing process. The assembly of the different parts is easily performed by the surgeon. In particular embodiments, the correct position of the bones for healing is ensured by the patient-specific character of each of the positioning parts of the bone plate.

The present disclosure further relates to methods for generating bone plates providing a tailored and defect-specific approach as each bone plates is made on the basis of the specific defective bone at hand and its envisaged repair.

Typically, the bone plate is developed by first generating a two dimensional (2D) or three dimensional (3D) model of the bone defect or envisaged osteotomy based on one or more images thereof, generating a 2D or 3D model of the envisaged repair of the bone defect or result of the osteotomy and generating a bone plate matching or corresponding to at least part of the surface of the bone fragments surrounding the area. Optionally, the bone plate is further provided with positioning elements. In further particular embodiments, the bone plate is provided with openings for fixation elements.

Accordingly, herein disclosed are methods of making a bone plate for fixing a bone defect, the method comprising the steps of: generating a 2D or 3D model of the bone defect or envisaged osteotomy based on one or more images of the bone and the surgical plan; designing based on said 2D or 3D model a model corresponding to the envisioned repair of said bone defect/envisaged result of the osteotomy; generating a bone plate with a rigid structure based on the information above comprising: one or more patient-specific features matching or corresponding to the surface of a bone fragment in the area close to the defect or osteotomy, and fixation features in areas suitable for fixing the bone plate to each of said bone fragments.

More particularly the methods for making a bone plate for fixing a bone defect may further comprise steps of returning to the model of the bone fragments prior to the envisaged repair (the original position of the bone fragments), taking into account the axis depth of the positioning and/or fixation elements of said bone plate, and generating a guide comprising drill-guides for drilling holes in to the bone fragments to receive the positioning and/or fixation elements of said bone plate. More particularly, said drill holes are predrill screw holes.

Thus, the methods as disclosed herein rely on one or more images of the bone defect or of the bone for which osteotomy is envisaged. In particular embodiments, the methods as disclosed herein include the step of taking images of the bone or bone defect. The images may be any type of image that can be used to create a 2D or 3D image or model of said envisaged repair of the bone or result of the osteotomy. It is not required that the images are of the entire patient. Indeed, typically, only part of the patient is reflected in the image, provided that this part also includes the area of the bone defect.

In particular embodiments, the images are 2D or 3D images. The images can be taken using any type of imaging apparatus or imaging technique which allows imaging or scanning the defective object in an accurate manner. These may include equipment such as cameras and scanners for industrial, household or medical use. In particular embodiments the imaging techniques and appliances used are typical medical imaging tools such as, but not limited to radiography, X-ray, ultrasound or fluoroscopy for 2D images and computer tomography (CT) scans, magnetic resonance imaging (MM) scans for 3D images. It is noted that from a combination of 2D images a 3D model can be constituted (according to U.S. 61/579,927 which is incorporated herein by reference). A summary of medical imaging has been described in "Fundamentals of Medical imaging", by P. Suetens, Cambridge University Press, 2002.

The term "medical imaging" as used herein refers to techniques and processes used to create images of the human or animal body (or parts and function thereof), typically for clinical purposes (medical procedures seeking to reveal, diagnose or examine disease) or medical science (including the study of normal anatomy and physiology).

Based on these images, a 2D or 3D model of the objects defective region is made. This 2D or 3D model allows a detailed analysis of the bone defect to determine the actual size and shape of the defect. The examination of the defect allows the reconstitution of the bone defect to its original position and/or the provision of the desired repair of the defect.

In particular embodiments, the methods involve performing virtual surgery on the defective bone to identify the defect site and determining the shape and/or form parameters of the defect or of the structure necessary to fix the defect. Based thereon, a model corresponding to the envisioned repair of said bone defect or osteotomy is generated. This can be obtained by manual designing based on anatomical knowledge. This involves determining the optimal position of the remaining elements relative to each other. Where the bone is a long bone, typically, the defect or osteotomy will generate two parts which need to be fixed in a specific position relative to each other. In other embodiments, such as fractures of the skull, the optimal position of multiple pieces may need to be determined.

In a next step the bone plate is generated based on the model corresponding to the envisioned repair of said bone defect or envisaged osteotomy. In particular embodiments, the bone plate is designed to comprise patient-specific features matching or corresponding to the surface of said model for one or more, and typically for each of the bone fragments. Additionally, the positions of the different positioning elements and openings for fixation elements (also referred to herein as fixation features) corresponding to suitable positions in each of the bone fragments which are to be fixed to each other is also determined. The methods as disclosed herein are envisaged e.g. in the context of orthopedic surgery. The model will allow the identification of areas on the bone fragments (typically in the vicinity of the defect) that are suitable for fixing and/or attaching the bone plate.

The bone plate can be made based on the information for these different features.

Typically, the methods allow the generation of a specifically fitting bone plate. Most particularly, the methods envisage making the bone plate in one piece or in separate detachable parts. Methods of manufacturing will be detailed below.

The step of generating said bone plate may thus include designing a model of a bone plate or an image thereof. The design of the bone plate may further be provided on an information carrier or can be sent to a manufacturing facility for the manufacturing of the bone plate or parts thereof. Thus, in particular embodiments, the methods as disclosed herein include manufacturing the bone plate or parts thereof.

As detailed above, the methods envisage the generation of a bone plate comprising one or more surfaces that fit specifically with the bone fragment(s). In particular embodiments, the bone plates may comprise one or more free-form structures fitting at least part of the surface of the bone fragments. The term "free-form structure" as used herein refers to a structure having an irregular and/or asymmetrical flowing shape or contour, more particularly fitting at least part of the contour of the bone fragments. Thus, in particular embodiments, the free-form structure is a free-form surface, as described above. A free-form surface refers to an (essentially) 2D shape contained in a 3D geometric space. Indeed, as will be detailed below, such a surface can be considered as essentially 2D but may have a varying thickness. Typically, the free-form structure or surface is characterized by a lack of rigid radial dimensions, unlike regular surfaces such as planes, cylinders and conic surfaces. Free-form surfaces are known to the skilled person and widely used in engineering design disciplines. Typically non-uniform rational B-spline (NURBS) mathematics is used to describe the surface forms; however, there are other methods such as Gorden surfaces or Coons surfaces. The form of the free-form surfaces are characterized and defined not in terms of polynomial equations, but by their poles, degree, and number of patches (segments with spline curves). Free-form surfaces can also be defined as triangulated surfaces, where triangles are used to approximate the 3D surface. Triangulated surfaces are used in STL (Standard Triangulation Language) files that are known to a person skilled in CAD design. The free-form structures are structured such that they fit the surface of said object specifically, thereby giving the structures their free-form characteristics.

Typically, the bone plates are designed to comprise free-form structures, wherein said free-form structures are patient-specific, i.e. they are made to fit specifically in the anatomy of a certain (animal or human) body-part.

As used herein, the term "patient-specific features" relates to a feature such as a surface, which is designed, based on an individual patient's anatomy to include features that have a custom fit on a specific location in a specific patient. The use of the patient-specific features in the bone plates allows to ensure an improved or optimized accuracy of the positioning of the device and thus of the introduction of the anchoring device for each patient. Accordingly, the term "patient-specific device or surface" is used to refer to a custom-made device or surface specific to the individual patient's anatomy. In particular embodiments the bone plates may comprise at least one patient-specific element or surface that ensures a patient-specific fit on the anatomy of a patient. In particular embodiments, the patient-specific surface conforms to or is complementary with at least part of the patient's anatomy.

The step of manufacturing the bone plate envisaged in the context of the methods as disclosed herein typically involves methods that allow the generation of free-form objects according to a pre-determined design. In particular embodiments, the bone plate is manufactured at least partially by additive manufacturing.

Additive Manufacturing can be defined as a group of techniques used to fabricate a tangible model of an object typically using 3D computer aided design (CAD) data of the object. Currently, a multitude of Additive Manufacturing techniques is available, including stereolithography, Selective Laser Sintering, Fused Deposition Modeling, foil-based techniques, etc.

Selective laser sintering uses a high power laser or another focused heat source to sinter or weld small particles of plastic, metal, or ceramic powders into a mass representing the 3D object to be formed.

Fused deposition modeling and related techniques make use of a temporary transition from a solid material to a liquid state, usually due to heating. The material is driven through an extrusion nozzle in a controlled way and deposited in the required place as described among others in U.S. Pat. No. 5,141,680.

Foil-based techniques fix coats to one another by means of gluing or photo polymerization or other techniques and cut the object from these coats or polymerize the object. Such a technique is described in U.S. Pat. No. 5,192,539.

Typically AM techniques start from a digital representation of the 3-D object to be formed. Generally, the digital representation is sliced into a series of cross-sectional layers which can be overlaid to form the object as a whole. The AM apparatus uses this data for building the object on a layer-by-layer basis. The cross-sectional data representing the layer data of the 3-D object may be generated using a computer system and computer aided design and manufacturing (CAD/CAM) software.

The bone plate envisaged in the context of the present disclosure are thus typically made of material which is compatible with additive manufacturing and which is able to provide a sufficient stiffness to the free-form structure. Suitable materials include, but are not limited to polyurethane, acrylonitrile butadiene styrene (ABS), polycarbonate (PC), PC-ABS, polyamide, polyamide with additives such as glass or metal particles, methyl methacrylate-acrylonitrile-butadiene-styrene copolymer, resorbable materials such as polymer-ceramic composites, etc. Examples of commercially available materials are: DSM Somos® series of materials 7100, 8100, 9100, 9420, 10100, 11 100, 12110, 14120 and 15100 from DSM Somos; ABSplus-P430, ABSi, ABS-ESDI, ABS-M30, ABS-M30i, PC-ABS, PC-ISO, PC, ULTEM 9085, PPSF and PPSU materials from Stratasys; Accura Plastic, DuraForm, CastForm, Laserform and VisiJet line of materials from 3-Systems; Aluminium, CobaltChrome and Stainless Steel materials; Maranging Steel; Nickel Alloy; Titanium; the PA line of materials, PrimeCast and PrimePart materials and Alumide and CarbonMide from EOS GmbH.

A further aspect as disclosed herein relates to computer programs for carrying out the methods for generating the bone plates as disclosed herein. In particular embodiments, computer programs are provided, which, when run on a computer, generate the bone plates as disclosed herein. In particular embodiments the computer programs are adapted to perform the different steps of the methods as disclosed herein. In further embodiments, computer programs comprise software code adapted to perform the steps of the methods as disclosed herein. The data processing system or computer program particularly refer to computer aided design and manufacturing systems and programs such as CAD/CAM systems or programs. Said computer programs typically comprise tools for loading images of the object with the defect, tools for generating a 3D model of said bone defect based on the images, tools for generating a virtual element based on said 3D model and tools for designing the bone plate and optionally tools for instructing a manufacturing system to manufacture the bone plate according to the generated design.

As illustrated above, methods are disclosed for fixing a bone defect making use of the bone plates described herein. In particular embodiments such methods comprise providing a bone plate as described herein, such as by performing the methods as described herein above. The methods then comprise the step of placing the bone plate on the defective bone.

The provision of patient-specific or, more particularly, defect-specific bone plates can overcome certain problems associated with existing procedures for the repair of bone defects. Thus in particular embodiments, disclosed herein are bone plates and methods for making such bone plates for fixing a defect on an anatomical part. Thus, according to this aspect, orthopedic bone plates for fixing a defect in an anatomical part are provided, comprising (1) a positioning element for providing the first fixation of the bone plate onto the bone, (2) openings through which bone fixation elements are inserted into the bone to definitely anchor the bone plate to the target portions of the bone and (3) one or more patient-specific features ensuring the correct position of the bone plate onto the bone defect.

In addition, according to this aspect, methods for providing bone plates for fixing a defect on an anatomical part, more particularly a bone are provided, which methods comprise the steps of: generating a 2D or 3D model of the bone defect based on one or more medical images of the defective region of the anatomical part; designing based on said 2D or 3D model a model corresponding to the envisioned repair of said bone defect; generating a bone plate corresponding to the envisioned repair of said bone defect such that said bone plate comprises patient-specific features matching or corresponding to the surface of said model and the positions of the different positioning elements and openings for fixation elements; and making said bone plate based on said design.

In particular the bone plate is an orthopedic structure for use as an implant. The bone plate may comprise means allowing fixation to the patient's anatomical part in a region not affected by the defect. The bone plate provides structural strength during the healing process.

In these embodiments, the bone plates are typically made of biocompatible material. The orthopedic bone plates as described herein and the methods for making them disclosed herein have the advantage that the implants are made and ready for use prior to surgery, whereas current devices are generic and do not match with the patient's anatomy leading to more complex surgery. Also, the geometry of the orthopedic bone plate is determined in advance and based on the patient's specific situation, thereby providing a perfect fit, resulting in a better, faster and more accurate healing process. Also, the proper design of orthopedic bone plate is considered as one of the most important aspects for the success of the surgical intervention. Time spent before surgery evaluating the exact dimensions of the bone defect and then custom design of the implant has numerous advantages. Donor site pain and morbidity is eliminated or reduced with maximal use of synthetic replacement parts. Operative times can be reduced significantly, often cutting the length of an operation in half.

In yet a further aspect, methods for performing a surgical procedure on an anatomical part using the patient-specific bone plate are provided as described herein. The method comprises: a) drilling one or more holes into the bone or bone fragments according to a preoperative plan for the re-alignment of the bone fragments; b) inserting into at least one of said holes at least one of the positioning elements of a bone plate or bone plate assembly, thereby fitting at least part of the bone plate or bone plate assembly to the anatomical part; c) aligning the bone fragments and positioning the bone fragments into the position required for optimal healing; and; d) fixating the bone plate onto the bone fragment(s) by inserting fixating elements into the bone through fixation features (e.g. holes) on the bone plate, thereby securing the bone fragments in said required position.

The present method for performing a surgical procedure may further comprise the step of using the partially inserted bone plate of step b) as a hinge for aligning the bone defect in step c).

Typically, the present method for performing a surgical procedure further comprises the step of sterilizing the bone plate before fitting the bone plate to the anatomical part.

In certain embodiments, the present method for performing a surgical procedure further comprises the step of using a surgical guide to drill one or more holes into the bone fragments and/or to perform osteotomy on the anatomical part.

In yet a further aspect, kits are provided comprising tools for performing at least part of the surgical procedure. The kit typically comprises a patient specific bone plate as disclosed herein and a guide. More particularly for use in the placement of the bone plate envisaged herein, the guide may be a guide for drilling holes corresponding to the positioning elements of the bone plate as disclosed herein. In particular embodiments this implies that the guide is also patient-specific and allows the drilling of holes according to a pre-determined surgical plan for the placement of the bone plate. However, it may also be envisaged that the kit comprises the same or a different guide which serves as a cutting guide for performing the osteotomy. Indeed, the use of bone plates as envisaged herein typically involves performing osteotomy to allow repositioning of the bone-parts. In particular embodiments, the kit comprises a guide which is a drill guide and/or a cutting guide for performing the osteotomy. The kit may additionally or alternatively comprise external positioning elements and/or fixation elements for further fixating the bone plate into the correct position.

The present disclosure will be illustrated by the following non-limiting embodiments.

EXAMPLES

Figure 1:
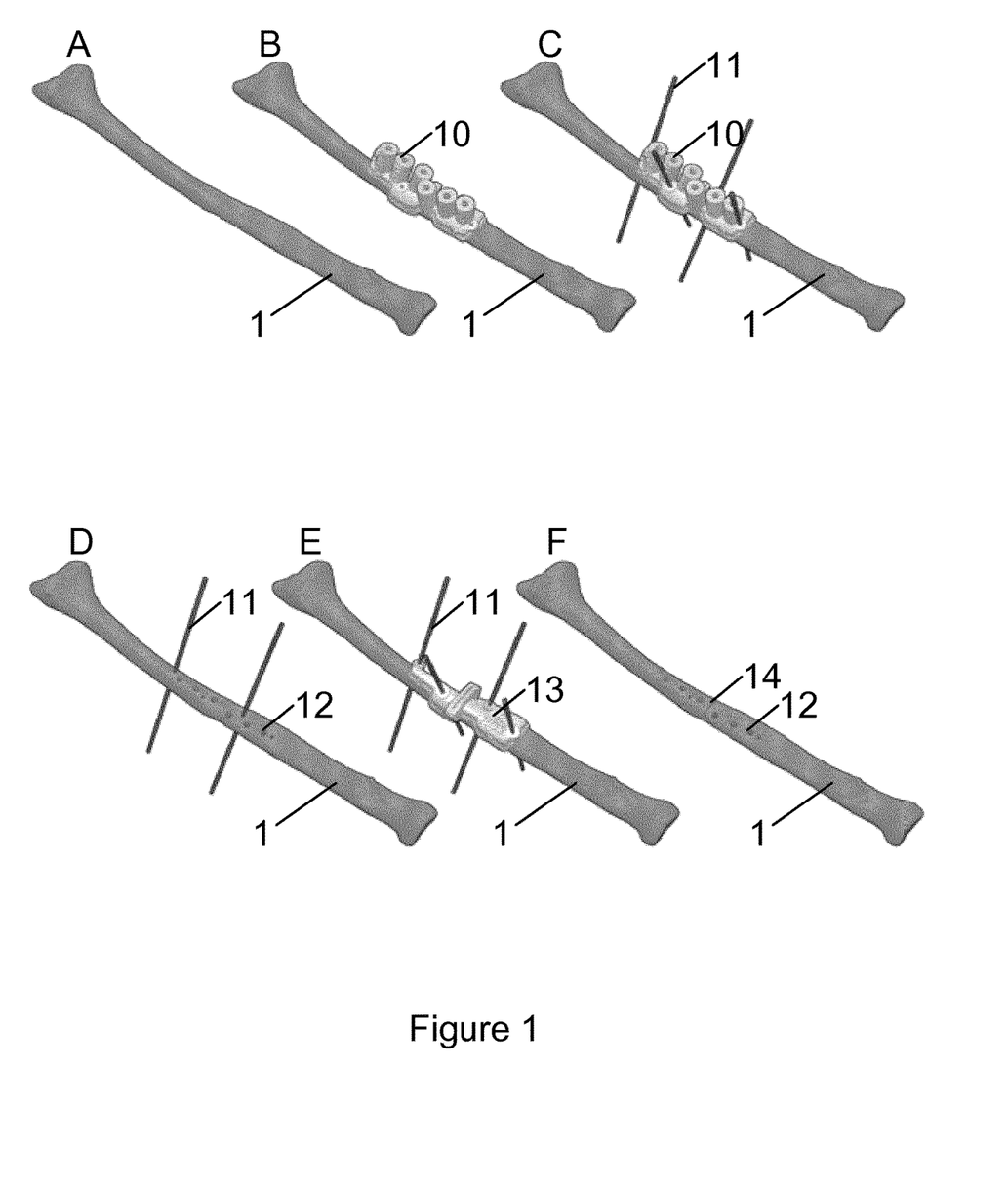
FIG. 1 illustrates an exemplified procedure for conducting a bone osteotomy.

FIG. 1 illustrates an exemplary embodiment where the different steps of a bone osteotomy are illustrated using guides and bone plates which are manufactured according to a pre-operative plan. A bone (1) is provided with a drill and/or cutting guide (10), which is used for drilling a number of holes in the bone (1) at predetermined positions.

The drill guide comprises holes for introducing K-wires. After introduction of the K-wires (11) the drill guide (10) is removed (while the K-wires remain in place. A cutting guide (13) is put in place, using the K-wires for guidance and further K-wires are introduced and the bone osteotomy (14) is performed. The guide and K-wires can then be removed.

Figure 2:
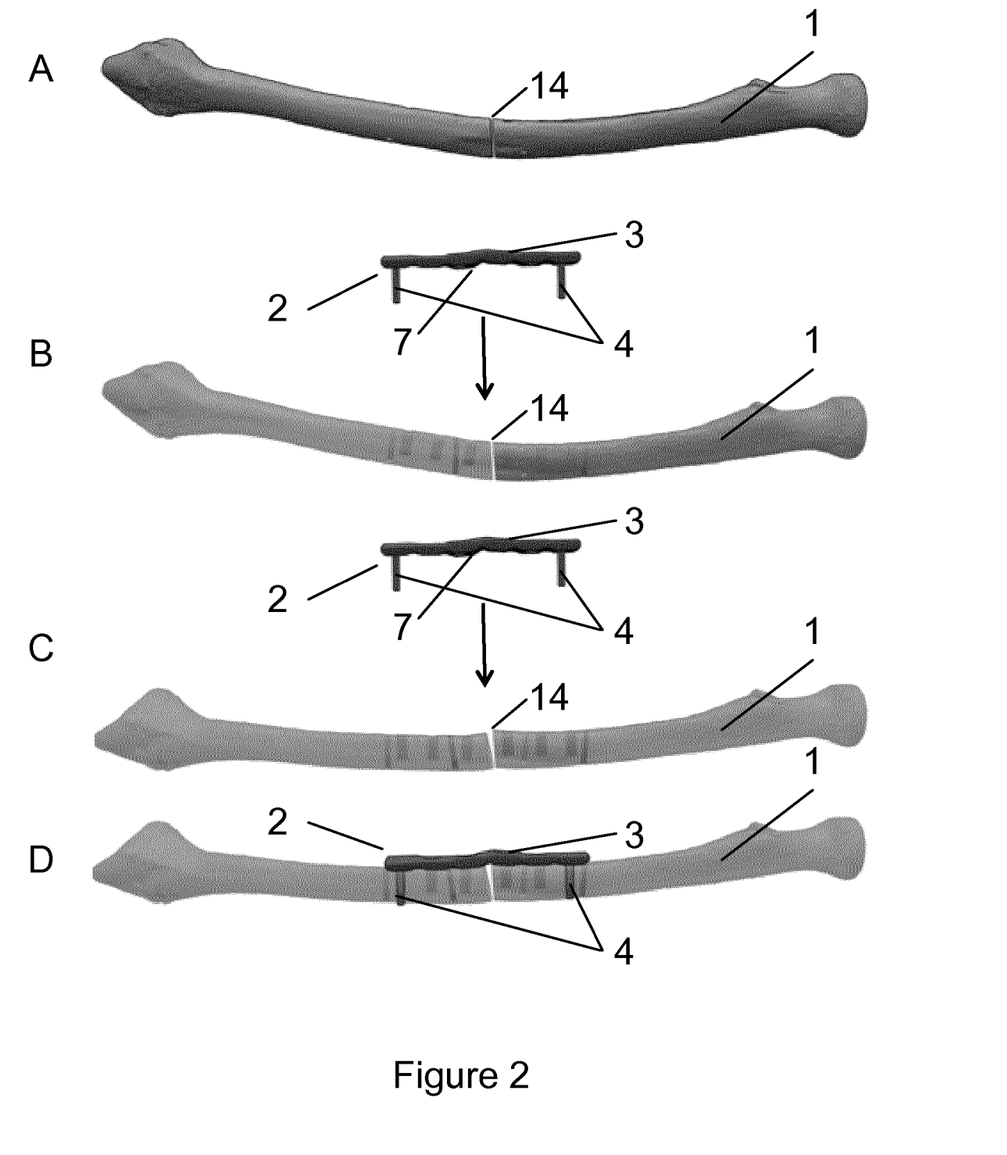
FIG. 2 illustrates the placement of a bone plate on a bone according to a particular embodiment.

FIG. 2 illustrates a specific embodiment where the different steps of positioning a bone plate are illustrated. A bone which has undergone a bone osteotomy (e.g. as illustrated in FIG. 1) is repositioned (from B to C) and a bone plate (2) having a supporting structure (3), a patient-specific part (7) and two pin-like positioning elements (4) is positioned onto the bone fragments, thereby positioning the bone fragments into a correct position for healing.

Figure 3:
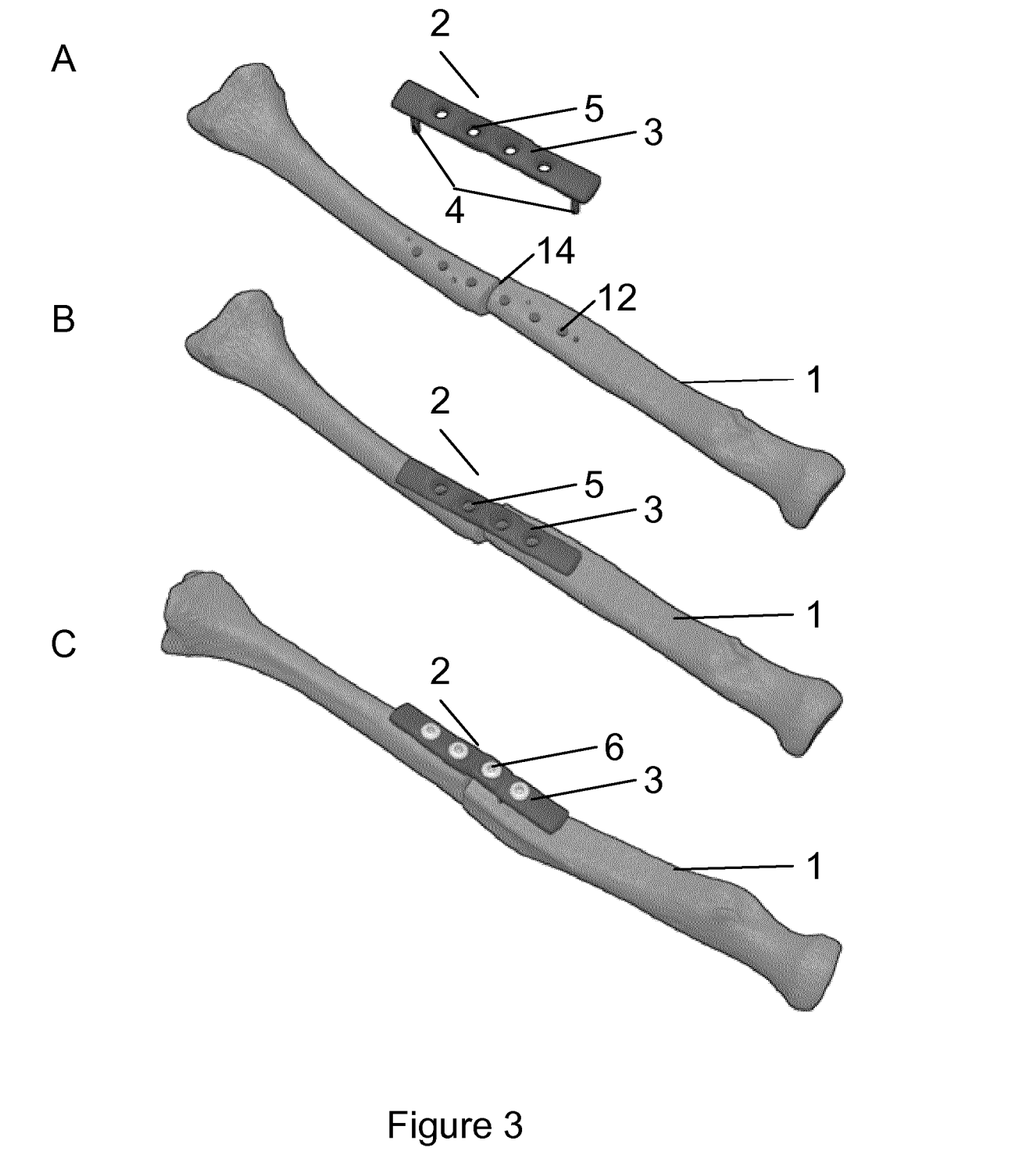
FIG. 3 illustrates the placement of a bone plate on a bone according to a particular embodiment.

FIG. 3 illustrates a specific embodiment where the different steps of positioning a bone plate are illustrated. A bone which has undergone a bone osteotomy or fracture is provided with a bone plate (2). Using the bone plate the correct position for healing is obtained and this correct healing position is fixated using fixation elements (6).

Figure 4:
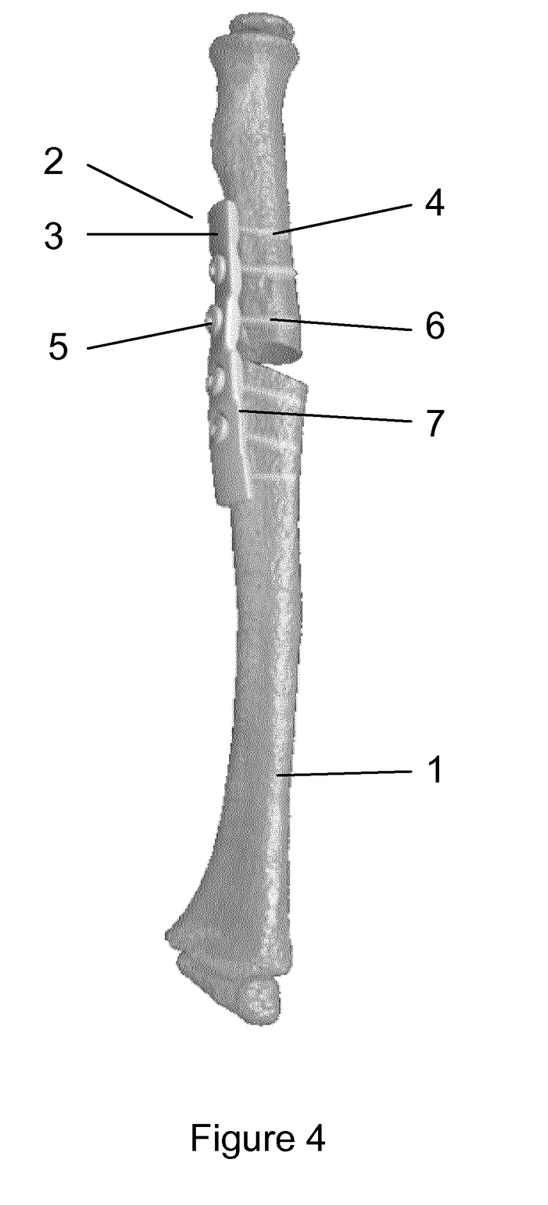
FIG. 4 illustrates an embodiment of a bone plate positioned on a bone.

FIG. 4 illustrates a specific embodiment of an orthopedic bone plate according to a particular embodiment. A fractured bone (1) has been repositioned into the correct healing position and this position is maintained using a bone plate (2) according to a particular embodiment. The bone plate (2) is provided with a supporting structure (3) which comprises positioning elements (4) for providing the first fixation of the bone plate onto the bone, fixation features (5) through which bone fixation elements (6) are inserted into the bone to definitely anchor the bone plate to the target portions of the bone and one or more patient-specific features (7) ensuring the correct position of the bone plate onto the bone defect. The orthopedic bone plate as illustrated in FIG. 4 can be used for the healing of large bone defects in long bones such as the femur, humerus or tibia. The implants are structurally stable and will not resorb or change their shape over time.

What is claimed is:

1. Method for designing a model of a bone plate comprising the steps of:
   generating a 2D or 3D model of a bone defect or envisaged osteotomy based on one or more images of a bone and a surgical plan;
   designing, based on said 2D or 3D model, a model of an envisioned repair of said bone defect or result of the envisaged osteotomy;
   designing a model of a bone plate with a rigid structure or supporting element based on the model of the envisioned repair of said bone defect or result of the envisaged osteotomy, the model of the bone plate comprising:
   a) one or more patient-specific features comprising at least a portion of a surface of the rigid structure or supporting element intended for placement on the bone matching a surface of a bone fragment in an area close to the bone defect or envisaged osteotomy,
   b) one or more fixation features of which the position and/or orientation is such that fixation elements will enter the bone in areas suitable for fixing the bone plate to said bone fragment, and
   c) one or more positioning elements extending from the surface of the rigid structure or supporting element, wherein the one or more positioning elements are pins or pegs, and wherein said one or more positioning elements are not detachable from the bone plate including the one or more patient-specific features; and
   designing a model of a guide for drilling holes in the bone in positions matching positions of the one or more positioning elements.

2. The method of claim 1, wherein the one or more positioning elements are non-threaded structures.

3. The method of claim 1, wherein said one or more positioning elements are provided on said bone plate so as not to be parallel to each other.

4. The method of claim 1, wherein said one or more patient-specific features comprise at least two patient-specific features, each matching a surface on one of two bone fragments which are to be fixed together.

5. The method of claim 1, wherein said rigid structure or supporting element has a varying thickness.

6. The method of claim 5, wherein the thickness of the rigid structure or supporting element is locally increased around an osteotomy or fracture plane.

7. The method of claim 1, wherein the one or more positioning elements comprise at least two positioning elements.

8. The method of claim 1, wherein the bone plate is provided in two or more separate parts, each comprising at least one of the one or more fixation features, which can be combined and attached to each other to form a one-piece bone plate after placement on bone fragments and positioning of the bone fragments in a desired position.

9. The method of claim 1, wherein a position and/or orientation of the one or more positioning elements is such that the one or more positioning elements will enter the bone.

* * * * *